US011812996B2

(12) United States Patent
Benoît

(10) Patent No.: US 11,812,996 B2
(45) Date of Patent: Nov. 14, 2023

(54) PLUG FOR BONE TISSUE

(71) Applicant: 9384-4934 QUEBEC INC., Montreal (CA)

(72) Inventor: Benoît Benoît, Laval (CA)

(73) Assignee: 9384-4934 QUEBEC INC., Montreal (CA)

( * ) Notice: Subject to any disclaimer, the term of this patent is extended or adjusted under 35 U.S.C. 154(b) by 198 days.

(21) Appl. No.: 16/624,519

(22) PCT Filed: Aug. 2, 2018

(86) PCT No.: PCT/CA2018/050950
§ 371 (c)(1),
(2) Date: Dec. 19, 2019

(87) PCT Pub. No.: WO2019/023807
PCT Pub. Date: Feb. 7, 2019

(65) Prior Publication Data
US 2020/0146722 A1    May 14, 2020

Related U.S. Application Data

(60) Provisional application No. 62/540,972, filed on Aug. 3, 2017.

(51) Int. Cl.
| A61B 17/68 | (2006.01) |
| A61B 17/17 | (2006.01) |
| A61B 17/72 | (2006.01) |
| A61B 17/90 | (2006.01) |

(52) U.S. Cl.
CPC ........ *A61B 17/686* (2013.01); *A61B 17/1764* (2013.01); *A61B 17/72* (2013.01); *A61B 17/90* (2021.08)

(58) Field of Classification Search
CPC ... A61B 17/68; A61B 17/686; A61B 17/1764; A61B 17/154; A61B 17/155; A61B 17/90; A61B 17/72
USPC .................................................. 606/315, 62
See application file for complete search history.

(56) References Cited

U.S. PATENT DOCUMENTS

| 4,007,494 A | 2/1977 | Sauer |
| 4,245,359 A | 1/1981 | Stuhmer |
| 5,100,405 A | 3/1992 | McLarin |
| 5,522,894 A | 6/1996 | Draenert |
| 5,782,917 A | 7/1998 | Carn |

(Continued)

FOREIGN PATENT DOCUMENTS

| AU | 2002234112 B2 | 12/2006 |
| JP | H0674116 U | 10/1994 |
| WO | 01/70136 | 9/2001 |

OTHER PUBLICATIONS

Extended European Search Report for corresponding European Application No. 18840780.3 dated Mar. 24, 2021.

(Continued)

*Primary Examiner* — Eduardo C Robert
*Assistant Examiner* — Christina Negrellirodriguez
(74) *Attorney, Agent, or Firm* — ANDRUS INTELLECTUAL PROPERTY LAW, LLP

(57) ABSTRACT

A cylindrical plug to close a femoral opening drilled in a femur to receive an intramedullary cutting guide, to prevent bleeding from the opening after removal of the intramedullary cutting guide from the opening.

17 Claims, 5 Drawing Sheets

(56) References Cited

U.S. PATENT DOCUMENTS

| | | | |
|---|---|---|---|
| 6,019,761 A | 2/2000 | Gustilo | |
| 6,752,833 B2 | 6/2004 | Hesseling et al. | |
| 2006/0030940 A1 | 2/2006 | Schmieding | |
| 2009/0312841 A1 | 12/2009 | Lalonde | |
| 2010/0042215 A1* | 2/2010 | Stalcup | A61B 17/866 606/86 R |
| 2010/0082072 A1* | 4/2010 | Sybert | A61B 17/686 606/86 R |
| 2013/0184820 A1* | 7/2013 | Schwartz | A61F 2/4618 623/14.12 |
| 2014/0094859 A1* | 4/2014 | Reed | A61B 17/863 606/315 |

OTHER PUBLICATIONS

International Search Report and Written Opinion for International Application No. PCT/CA2018/050950 dated Oct. 29, 2018.
Vulcano, E et al. 'Femoral Bone Plug in Total Knee Replacement.' Orthopedics. 2015 vol. 38(10): pp. 617-618.
Examination Report for corresponding Australian Patent Application No. 2018310776 dated Jun. 23, 2020.
"Types of Allen Keys and Their Uses". Big Speedy Fixings. 2023. Accessed at https://www.speedyfixings.com/types-of-allen-keys-and-their-uses/ on Sep. 13, 2023.
Examination Report for New Zealand Patent Application No. 760029, dated Aug. 17, 2023.

* cited by examiner

PLUG FOR BONE TISSUE

CROSS-REFERENCE TO RELATED APPLICATIONS

This application is the U.S. national stage application of International Application PCT/CA2018/050950, filed Aug. 2, 2018, which international application was published on Feb. 7, 2019, as International Publication WO 2019/023807 A1 in the English language. The International Application claims priority of U.S. Provisional Patent Application No. 62/540,972 filed Aug. 3, 2017.

FIELD OF THE INVENTION

The present disclosure relates to a plug to seal a bone cavity and the use of the plug to seal the cavity.

BACKGROUND

Total knee replacement (TKR) is a widespread surgery in western countries recommended for patients who experience severe destruction of their knee joint. In 2010, approximately 700,000 TKRs were performed in the United States only. By 2030, it is projected that over 3.5 million procedures will be performed annually.

During the procedure, the femoral canal is opened by drilling a hole in the femur using a mesh having a diameter generally between 8 and 12 mm. This femoral opening is subsequently used to position an intramedullary cutting guide as shown in FIGS. 1a and 1b. This cutting guide ensures the proper orientation and position of the cut of the femoral bone for subsequent installation the femoral prosthesis component.

The femoral opening created during the procedure allows blood to flow from the femoral canal to the surgical area both during and after the surgical procedure which in turn contributes to the formation of hematomas in the knee joint. This contributes to pain and causes a drop in hemoglobin level which can lead to systemic complications, increased risks of infection and/or require blood transfusions.

Currently, in order to reduce the bleeding, some surgeons may attempt to seal the femoral opening by impacting small fragment of bone cut during the surgery to create a bone plug, as shown in FIG. 2. Performing this procedure takes times and the cutting of bone fragments may damage surgical gloves which in turn increases the risks of infection and contamination. Furthermore, the bone plug being impacted into the femoral hole may be subsequently dislodged and may cause mechanical motion issues in the knee joint. Finally, this technique, although reducing bleeding from the femoral canal, does not seal the femoral opening in such a way that bleeding is eliminated.

There is accordingly a need to provide a plug for the femoral canal discussed above that alleviates at least some of the problems of the bone plugs currently used.

SUMMARY

According to various aspects of the present disclosure, there is provided a use of a substantially cylindrical plug to close a femoral opening drilled in a femur to receive an intramedullary cutting guide, to prevent bleeding from the opening after removal of the intramedullary cutting guide from the opening.

According to another aspect of the present disclosure, there is provided a use pf a drill to drill an opening in a femur; intramedullary cutting guide configured for insertion into the femur; a substantially cylindrical plug having a size selected according to a size of the opening to close the opening subsequent a removal for the intramedullary cutting guide from the opening.

According to a third aspect of the present disclosure, there is provided a method for performing a knee surgery, comprising the steps of drilling a femoral opening in the femur; positioning an intramedullary cutting guide in the opening; cutting the femur; removing the intramedullary cutting guide from the opening; providing a substantially cylindrical plug selected according to a size of the opening in the femur; inserting the plug in the femoral opening to close the opening and prevent bleeding from the opening; and performing any additional step to complete the knee surgery.

According to a fourth aspect of the present disclosure, there is provided a plug configured to seal a femoral opening drilled in a femur to position an intramedullary cutting guide, the plug including a substantially cylindrical body for insertion into the opening to engage bone surrounding the opening in order to create a seal to prevent blood loss through the opening.

According to a fifth aspect of the present disclosure, there is provided a kit comprising an intramedullary cutting guide including a member configured for insertion in a femoral opening drilled in a femur to position the intramedullary cutting guide, the kit including a plug having a generally cylindrical body, the plug having a transverse dimensions selected according to a transverse dimensions of the member in order to create close the opening after removal of the member from the opening.

These and other aspects of the present disclosure will now become apparent to those of ordinary skill in the art upon review of the following description of embodiments in conjunction with the accompanying drawings.

DETAILED DESCRIPTION

Figure 1A:
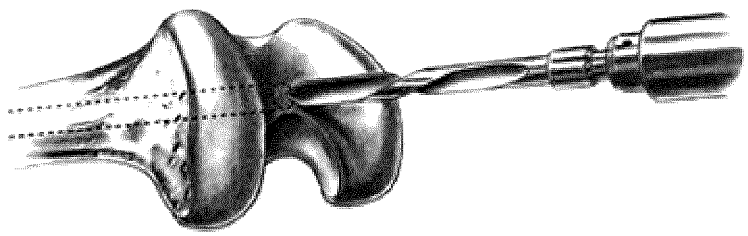
FIG. 1a shows an isometric view of a femur with a femoral opening (in dotted lines) to be drilled.
Figure 1B:
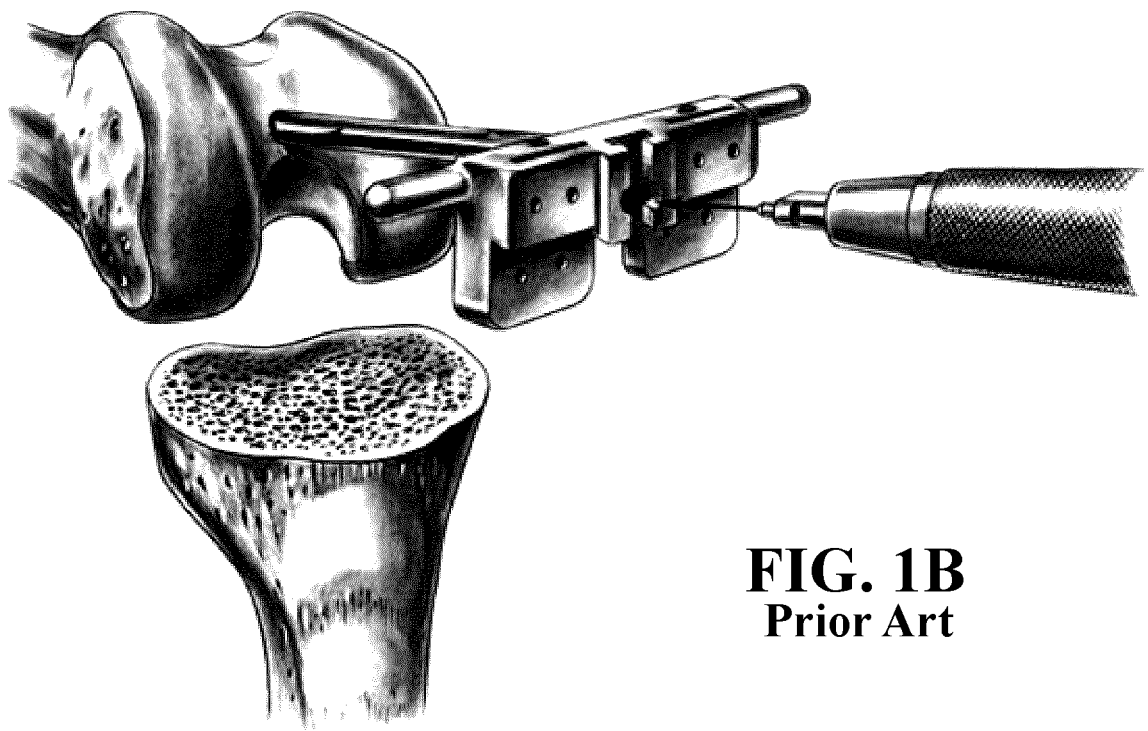
FIG. 1b shows an isometric view of an intramedullary cutting guide positioned into the femoral opening.
Figure 2:
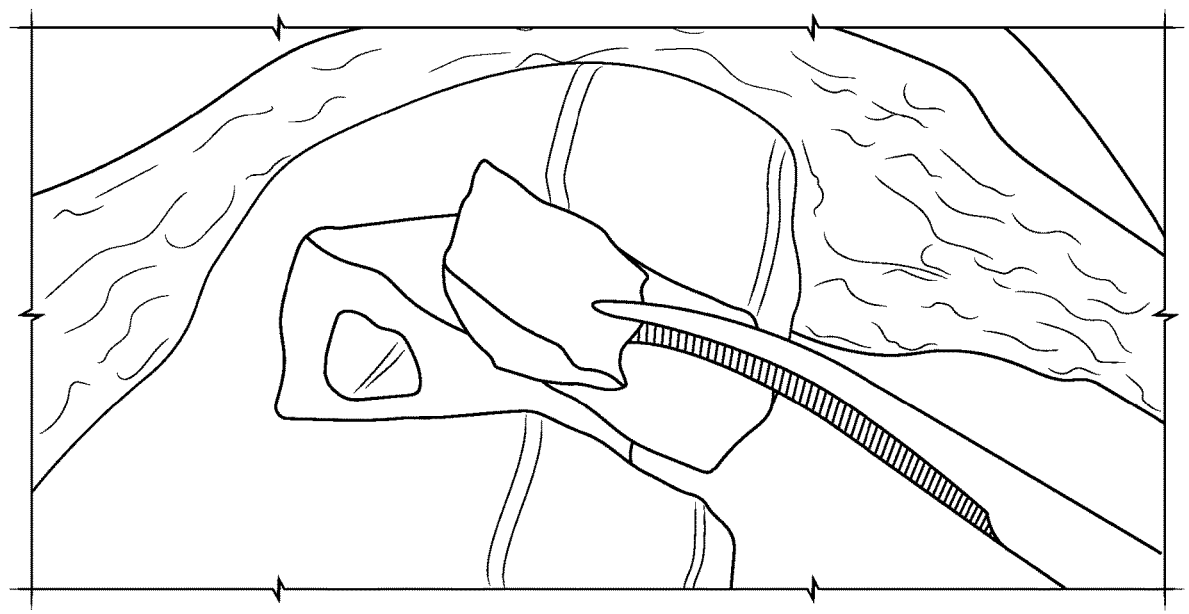
FIG. 2 shows a bone plug as currently used to be impacted in the femoral opening of FIGS. 1a and 1b without preventing bleeding from the femoral opening.
Figure 3:
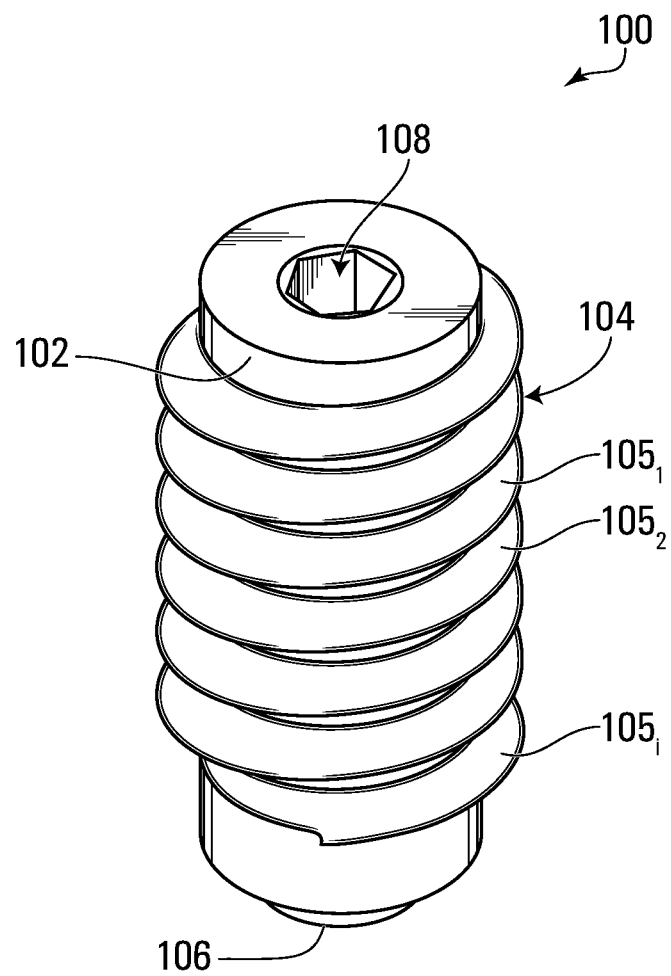
FIG. 3 shows an isometric view of a plug for a femoral opening in accordance with one non-limiting embodiment.

With reference to FIG. 1 there is provided a plug 100 according to a non-limiting embodiment of the present disclosure. The plug 100 may be of a screw type, consisting of a generally cylindrical body 102 having a lower portion and higher portion and featuring a helical thread structure 104 running at least in part alongside a periphery of the cylindrical body 102. The plug 100 may be of any other suitable type (i.e., not of a screw type) in other embodiments. The plug 100 is configured to be inserted inside a cavity in a bone, in this non-limiting embodiment via its lower portion.

The helical thread structure 104 may be configured to engage an internal wall of the cavity when the plug 100 is inserted inside the cavity and generally prevent any fluid communication between the anatomical regions facing the lower and higher portions of the cylindrical body 102, respectively, when inserted in the cavity. In this non-limiting embodiment, the cavity is a femoral opening drilled in the femur to position an intramedullary cutting guide. The cavity may notably be drilled during a TKR surgery. However, other cavities may be suitable in other embodiments and the plug 100 may be configured to be inserted in a cavity during other surgical procedures such as, but not limited to, a revision of total knee prosthesis, a retrograde rodding of the femur and the likes. The helical thread structure 104 may comprise a series of parallel ridges $105_1$-$105_i$ generally extending about a periphery of the cylindrical body 102. In this embodiment, the ridges $105_1$-$105_i$ comprise a single helix that spirals about the periphery of the cylindrical body 102. In other embodiments, the ridges $105_1$-$105_i$ may comprise separate, discrete parallel bands around the periphery of the plug 100. The helical thread structure 104 may have any other suitable configuration in other embodiments. In yet further embodiments, the plug 100 may not comprise a helical thread structure 104, as further disclosed below.

The plug 100 may comprise a chamfered edge 106 at the bottom portion of the cylindrical body 102, the chamfered edge 106 being configured to facilitate entry and positioning of the plug 100 in the cavity. In other embodiments, the chamfered edge 106 may be absent and/or the bottom portion of the cylindrical body 102 may comprise any suitable element to facilitate entry and positioning of the plug 100 in the cavity.

The plug 100 may comprise a socket 108 in the upper portion of the cylindrical body 102 configured for facilitating insertion of the plug 100 inside the cavity. In this non-limiting embodiment, the socket 108 may be of a traditional hex type socket or a 12-point torx type socket or any other suitable type of socket that enables a user to impart a rotational motion to the plug 100 inside the cavity. This contributes to the insertion of the helical thread structure 104 inside the walls of the cavity. The plug 100 may be inserted inside the cavity in any other suitable way (e.g., without imparting a rotational movement to the plug 100) in other embodiments.

Once inserted inside the cavity, the plug 100 is configured to generally prevent any fluid communication between the anatomical regions facing the bottom and the higher portions of the cylindrical body 102. That is, where the cavity is a femoral opening drilled in the femur to position an intramedullary cutting guide, the plug 100 is configured to generally prevent bleeding from the femoral canal inside the region of the knee joint. The plug 100 is also configured to be generally stable once inserted in the cavity, such that the plug 100 generally does not move laterally or vertically in the cavity and remains inside the cavity once inserted. That is, where the cavity is a femoral opening drilled in the femur to position an intramedullary cutting guide, the plug 100 is configured to generally remain in the femoral opening and to not be dislodged from the femoral opening.

The plug 100 has a diameter and a length generally configured to seal the cavity, which may be a femoral opening drilled in the femur to position an intramedullary cutting guide. In one non-limiting example, the cylindrical body 102 of the plug 100 may have a diameter comprised between 6 and 15 mm and a length between 10 and 30 mm. The cylindrical body 102 may have any other suitable diameter and/or length in other embodiments. In one embodiment, the cylindrical body 102 may have a diameter selected based on a diameter of a drill bit used to drill the femoral opening in the femur such that the cylindrical body has a diameter configured to ensure the stability of the plug 100 once inserted in the cavity, such that the plug 100 generally does not move laterally or vertically in the cavity and remains inside the cavity once inserted.

The chamfered edge 106 may have any suitable angle and size. The helical thread structure 104 may have any suitable dimension and configuration such as pitch, pitch diameter and angle of the ridges $105_1$-$105_i$.

In this non-limiting embodiment, the cylindrical body 102 is generally not hollow. In other non-limiting embodiments, the cylindrical body 102 may be generally hollow and configured to be inflated or mechanically deformed in order to make the plug 100 engage the cavity when the plug 100 is inserted in the cavity and generally prevent any fluid communication between the bottom portion and a higher portion of the cylindrical body 102 when inserted in the cavity. In this embodiment, the cylindrical body 102 may be configured to retain its inflated or mechanically deformed shape after being inflated or mechanically deformed. It is appreciated that in the configuration where the cylindrical body 102 may be generally hollow and inflatable or mechanically deformable, the plug 100 may not comprise a helical thread structure 104 and may not be inserted via a rotational motion to the plug 100 inside the cavity.

In this non-limiting embodiment, the plug 100 may be made of a metallic biocompatible material, such as a titanium or stainless steel alloy. The plug 100 may be made of any other suitable biocompatible material, metallic or non-metallic, in other embodiments. The plug 100 may also be made of a non-biological material such that the plug 100 is not made of bone tissue or any other bodily tissue. In other non-limiting embodiments, the plug may be made of any suitable biodegradable material.

The plug 100 may be a permanent plug. That is, the plug 100 may be configured to remain in the cavity. In other non-limiting embodiments, the plug 100 may be temporary, notably when the plug 100 is made of a biodegradable material.

In a non-limiting embodiment, the plug 100 may be used to seal a femoral opening drilled in the femur to position an intramedullary cutting guide. This may notably be the case during a TKR surgery. In other embodiments, the plug 100 may be used to seal a cavity in a bone during other surgical procedures such as, but not limited to, a revision of total knee prosthesis, a retrograde rodding of the femur and the likes.

Figure 4:
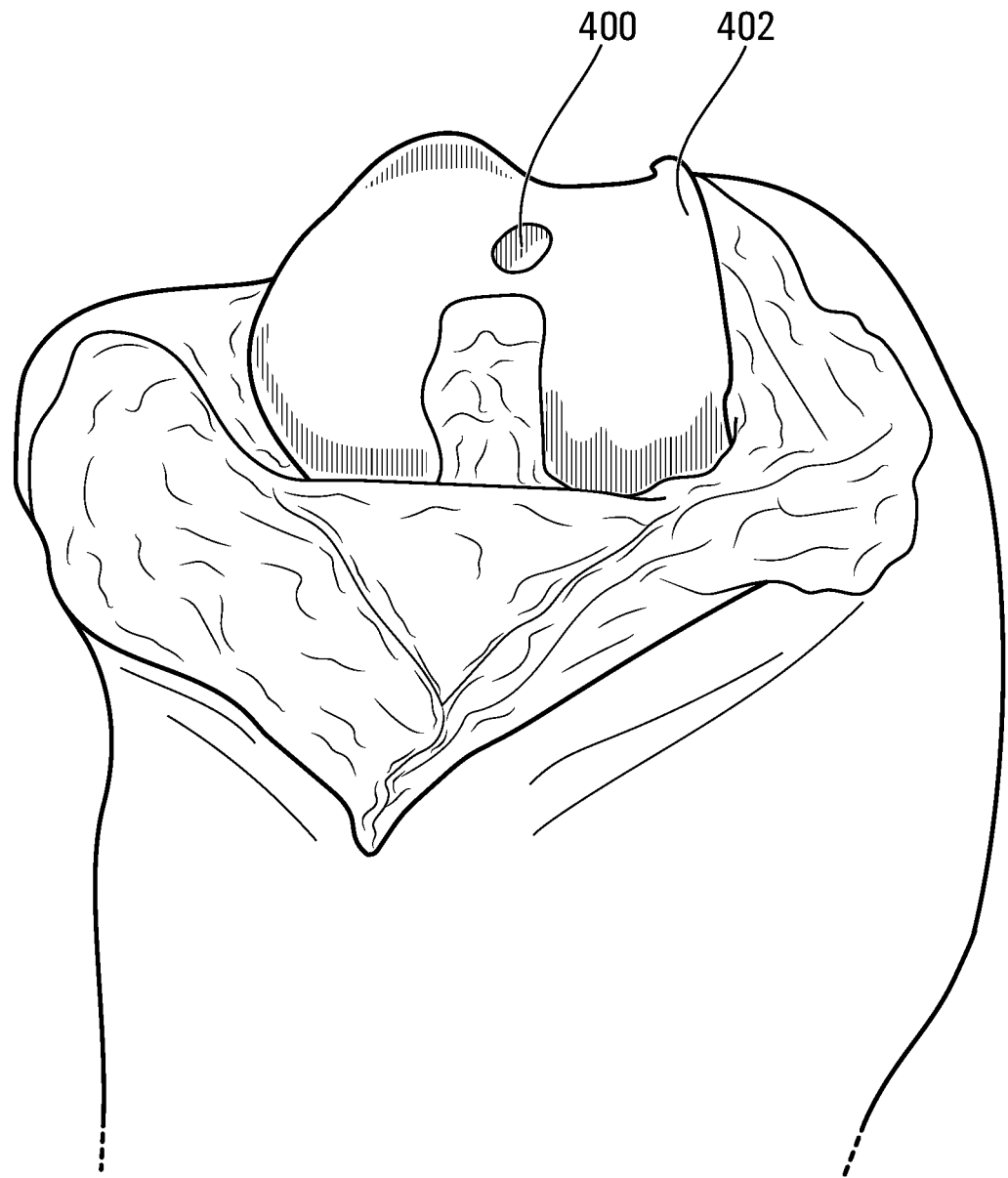
FIG. 4 shows a femoral opening drilled in the femur prior to positioning an intramedullary cutting guide during a TKR surgery.

With reference to FIG. 4, a step of TKR surgery is shown in which a femoral opening 400 has been drilled in the femur 402. The femoral opening is used at a subsequent step (not shown) to position an intramedullary cutting guide. The intramedullary cutting guide is then used to cut the femur 402 (not shown).

Figure 5:
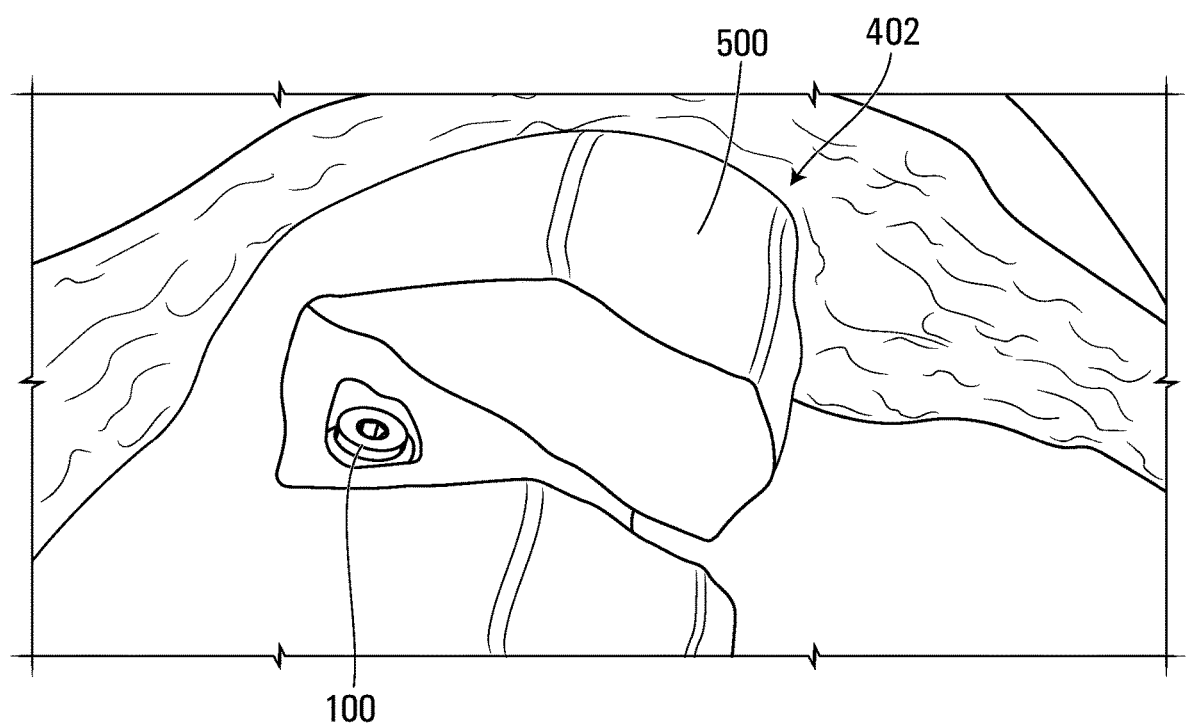
FIG. 5 shows the femoral opening of FIG. 4 being sealed by the plug after the femur has been cut during a TKR surgery in accordance with one non-limiting embodiment.

With further reference to FIG. 5, the cut portion 500 of the femur 402 is shown after the intramedullary cutting guide has been removed and with the plug 100 sealing the femoral opening 400, the plug 100 generally preventing bleeding from the femoral canal inside the region of the knee joint. It is appreciated that the femoral opening 400 is sealed with a minimum of handling required from the operating surgeon.

Certain additional elements that may be needed for operation of some embodiments have not been described or illustrated as they are assumed to be within the purview of those of ordinary skill in the art. Moreover, certain embodiments may be free of, may lack and/or may function without any element that is not specifically disclosed herein.

Any feature of any embodiment discussed herein may be combined with any feature of any other embodiment discussed herein in some examples of implementation.

In case of any discrepancy, inconsistency, or other difference between terms used herein and terms used in any document incorporated by reference herein, meanings of the terms used herein are to prevail and be used.

Although various embodiments and examples have been presented, this was for the purpose of describing, but not limiting, the present disclosure. Various modifications and enhancements will become apparent to those of ordinary skill in the art and are within the scope of the invention, which is defined by the appended claims.

The invention claimed is:

1. A method for preventing bleeding from a femoral opening drilled in a distal region of a femur forming part of a knee joint and having a medullary canal, the method comprising:
   drilling the femoral opening in the distal region of the femur thereby opening the medullary canal;
   positioning an intramedullary cutting guide in the femoral opening;
   cutting a portion of the distal region of the femur in accordance with the intramedullary cutting guide;
   removing the intramedullary cutting guide from the femoral opening; and
   inserting a femoral plug into the femoral opening to form a seal with bone tissue from the femur to prevent bleeding from the femoral opening into the knee joint, the femoral plug comprising:
     an elongated body sized for insertion into the femoral opening; and
     threads extending around at least a portion of the elongated body to engage bone surrounding the femoral opening to form a seal with the bone to prevent blood loss from the femoral opening into the knee joint;
   wherein inserting the femoral plug comprises;
   imparting a rotational motion to the femoral plug to engage the threads of the femoral plug with bone surrounding the femoral opening.

2. The method of claim 1, wherein the femoral opening is drilled in the distal region of the femur to position the intramedullary cutting guide during a total knee replacement surgery.

3. The method of claim 1, further comprising selecting a size of the femoral plug in accordance with at least one characteristic of the intramedullary cutting guide.

4. The method of claim 3, wherein the at least one characteristic of the intramedullary cutting guide is a diameter of a drill bit used to drill the femoral opening in the distal region of the femur.

5. The method of claim 1, wherein the femoral plug is made of a biocompatible material.

6. The method of claim 1, wherein the threads comprise a helical thread structure.

7. The method of claim 6, wherein the helical thread structure comprises a series of parallel ridges.

8. The method of claim 7, wherein the parallel ridges comprise a single helix that spirals about a periphery of the elongated body.

9. The method of claim 7, wherein the parallel ridges comprise discrete parallel bands around a periphery of the elongated body.

10. The method of claim 1, wherein the elongated body comprises a chamfered edge to facilitate the inserting of the femoral plug into the femoral opening.

11. The method of claim 1, wherein the femoral plug comprises a socket to facilitate the inserting of the femoral plug into the femoral opening.

12. The method of claim 1, wherein the femoral plug further comprises a tool-engaging portion configured to be engaged by a tool for driving the femoral plug into the femoral opening during the inserting.

13. The method of claim 1, wherein the threads of the femoral plug are integrally formed with the elongated body.

14. The method of claim 1, wherein the elongated body of the femoral plug is free of a longitudinally-extending through hole.

15. The method of claim 1, wherein the elongated body of the femoral plug is monolithic.

16. The method of claim 1, further comprising inflating the femoral plug to further engage the threads with the bone surrounding the femoral opening.

17. The method of claim 1, further comprising mechanically deforming the femoral plug to further engage the threads with the bone surrounding the femoral opening.

* * * * *